United States Patent
Lee

(10) Patent No.: US 11,782,010 B2
(45) Date of Patent: Oct. 10, 2023

(54) ELECTRODE FOR BIOSENSOR FOR NADH MEASUREMENT AND MANUFACTURING METHOD THEREFOR

(71) Applicant: KOREA RESEARCH INSTITUTE OF CHEMICAL TECHNOLOGY, Daejeon (KR)

(72) Inventor: Kyuhong Lee, Jeollabuk-do (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 563 days.

(21) Appl. No.: 16/959,506

(22) PCT Filed: Dec. 28, 2018

(86) PCT No.: PCT/KR2018/016829
§ 371 (c)(1),
(2) Date: Jul. 1, 2020

(87) PCT Pub. No.: WO2019/135556
PCT Pub. Date: Jul. 11, 2019

(65) Prior Publication Data
US 2021/0055251 A1 Feb. 25, 2021

(30) Foreign Application Priority Data
Jan. 2, 2018 (KR) .................. 10-2018-0000408

(51) Int. Cl.
*G01N 27/327* (2006.01)
(52) U.S. Cl.
CPC ................. *G01N 27/3277* (2013.01)
(58) Field of Classification Search
None
See application file for complete search history.

(56) References Cited

U.S. PATENT DOCUMENTS

| 5,081,014 A | 1/1992 | Brochot et al. |
| 8,518,572 B2 | 8/2013 | Kim et al. |
| 2005/0067303 A1 | 3/2005 | Wong et al. |

FOREIGN PATENT DOCUMENTS

| CN | 1821751 A | 8/2006 |
| CN | 104316585 A | 1/2015 |

(Continued)

OTHER PUBLICATIONS

Retna Raj et al. "Electrocatalytic sensing of NADH at an in situ functionalized self-assembled monolayer on gold electrode" Electrochemistry Communications 3 (2001): 633-638.

(Continued)

*Primary Examiner* — J. Christopher Ball
(74) *Attorney, Agent, or Firm* — RAPHAEL BELLUM PLLC

(57) ABSTRACT

The present invention relates to an electrode for a biosensor for NADH measurement and a manufacturing method therefor. An electrode manufactured by the method according to the present invention enjoys the advantages of stabilizing current flow during an electric polymerization reaction, making the contact angle of the modified material remarkably small to increase the efficiency of surface modification, and being reusable several times. In addition, when applied to a biosensor for NADH measurement, the electrode of the present invention maintains sensitivity and selectivity at a high level without interference and thus easily measures a target of interest even in blood or serum that necessarily requires a pretreatment process due to the existence of a trace amount of a material to be measured. In addition, when applied to a biosensor for NADH measurement, the electrode can measure cell viability in a continuous manner and in real time, which leads to the application thereof to the cell toxicity assay field, and enables the measurement of cell (Continued)

viability in apoptotic cells lacking the mitochondrial function.

15 Claims, 3 Drawing Sheets

(56) References Cited

FOREIGN PATENT DOCUMENTS

| | | | |
|---|---|---|---|
| JP | S60-043398 | A | 3/1985 |
| JP | S62-158496 | A | 7/1987 |
| JP | H11-075894 | A | 3/1999 |
| JP | 2004-233289 | A | 8/2004 |
| JP | 2005-517960 | A | 6/2005 |
| KR | 1020090045491 | A | 5/2009 |
| KR | 101067867 | B1 | 9/2011 |
| KR | 1020120085470 | A | 8/2012 |
| KR | 1020130121464 | A | 11/2013 |
| KR | 101809905 | B1 | 12/2017 |

OTHER PUBLICATIONS

Uzer et al., "Electrochemical Determination of Food Preservative Nitrite with Gold Nanoparticlesp-Aminothiophenol-Mlodified Gold Electrode", Int. J. Mol. Sci. 2016, 17, 1253; pp. 1-17.

ELECTRODE FOR BIOSENSOR FOR NADH MEASUREMENT AND MANUFACTURING METHOD THEREFOR

TECHNICAL FIELD

The present invention relates to an electrode for a biosensor and a method for manufacturing the same, and more particularly, to an electrode for a biosensor for measuring NADH (reduced form of nicotinamide adenine dinucleotide or reduced NAD) and a method for manufacturing the same.

BACKGROUND

With the advancement in biotechnology, the demand and need for faster and more accurate analysis techniques are gradually increasing. Of such analysis techniques, a lot of research has been conducted recently on biosensors. In particular, there is a steadily increasing demand for biosensors, which are bio-devices capable of sensing physical and chemical stimuli received from the outside with the application of electronic engineering by imitating biological functions. These biosensors are receiving attention because of their very high selectivity and sensitivity for the object to be measured.

A wide variety of research has been conducted on biosensors so far, and these biosensors can be divided into those using biomaterials from enzymes and fungi and from tissues of animals and plants. They can be divided into a part that recognizes specific molecules and causes physical and chemical changes in proportion to their concentration, and a part that converts chemical changes of these materials into electrical signaling sites. In particular, since such biosensors can selectively recognize specific molecules in a sample and do not need to perform separate purification, there exist advantages that the detection time is very short and the accuracy is very high.

Electrochemistry-based biosensors combine analysis capabilities of electrochemical methods with the specificity of biological recognition. In other words, by fixing or containing biospecific reagents, such as enzymes, antigens, antibodies, biochemical substances, and so on, onto the surface of an electrode, the phenomenon of biological recognition is detected by a change in electric current or potential. In such electrochemistry-based biosensors, the resistance of the electrode itself and the characteristics of the surface on which electrochemical reactions occur are very important.

On the other hand, maintaining the homeostasis of mitochondria, which are organelles of cells responsible for ATP synthesis required during life activities, is very important within life activities, and if any abnormalities occur in that, multiple diseases such as metabolic-related disorders, stroke, and so on can be caused at the same time. What is commonly and frequently used to check the function of the mitochondria corresponds to the coenzyme generated during respiration in the mitochondria. In particular, nicotinamide adenine dinucleotide (NAD) is one of the important coenzymes found in cells and is widely used for the TCA cycle and glycolysis in cell respiration, and the reduction potential stored in NADH corresponding to the reduced form of NAD is converted to ATP through an electron transport system or used for anabolic reactions.

Therefore, a lot of research focuses on the fundamental scientific application of the NADH reaction; however, the measurement of NADH in blood exhibits low sensitivity due to very strong interference, a significantly low selectivity, a very high rate of sample consumption, and a very complicated pretreatment process, in the case of the conventional absorption method, and accordingly, is difficult to measure conveniently. In addition, the WST-1 and MTT (3-(4,5-Dimethylthiazol-2-yl)-2,5-Diphenyltetrazolium Bromide) assays in the related art correspond to a method of injecting a chemical substance, followed by inducing a color reaction with an NADH factor to thereby measure the absorbance at specific wavelengths, but such a method is not suitable for continuous and real-time monitoring because it requires a large amount of sample, takes a long reaction time, and resolution is not good enough. Moreover, in order to measure NADH by an electrochemical method, it is necessary to induce an enzymatic reaction, or to add a mediator of the ions of ruthenium or cyanide that is a catalytic substance for actively transferring electrons, thereby measuring the oxidation-reduction current of NADH, but in this case, since the oxidation and reduction occur at a voltage value of 1000 mV or higher, there are disadvantages that the electrode surface is damaged to thereby make repetitive measurements impossible, and resolution is significantly reduced.

SUMMARY OF INVENTION

Technical Objects

The present inventors produced a step of varying the concentration of a solution for immersion when applying a voltage in the step of applying cyclic voltage-current in the process of modifying the surface of an electrode for a biosensor with 4-aminothiophenol, and thus found not only to significantly increase the modification efficiency but also to have high sensitivity and selectivity and to be reusable multiple times, thereby completing the present invention.

Technical Solution

The present invention provides a method for manufacturing an electrode for a biosensor, comprising:
a) washing the electrode with sulfuric acid;
b) after the electrode of said step a) is placed in 4-aminothiophenol (4-ATP) and cultured, immersing the electrode in a first solution and then applying a voltage; and
c) immersing the electrode of said step b) in a second solution and then applying a voltage.

In the present invention, the first solution in said step b) may be a phosphate buffer solution of a molar concentration of 90 mM to 100 mM.

Further, in the present invention, the second solution in said step c) may be a phosphate buffer solution of a molar concentration of 5 mM to 15 mM.

In the present invention, the voltage in said steps b) and c) may be applied by cyclic voltammetry.

Moreover, in the present invention, in said steps b) and c), said cyclic voltammetry may be to sweep a potential from 0.8 to −0.4 V.

Furthermore, in the present invention, the electrode may comprise one or more kinds selected from a group consisting of gold, aluminum, platinum, nickel, graphene, silver nanowire films, metal grids, and indium tin oxide.

In the present invention, the electrode for a biosensor may be for measuring NADH (reduced form of nicotinamide adenine dinucleotide).

An electrode for a biosensor for NADH measurement by the manufacturing method in accordance with the present invention is provided.

A biosensor comprising the electrode in accordance with the present invention is provided.

Hereinafter, an electrode for a biosensor for NADH measurement in accordance with the present invention will be described in detail.

An implementation of the present invention provides a method for manufacturing an electrode for a biosensor, comprising: a) washing the electrode with sulfuric acid; b) after the electrode of said step a) is placed in 4-aminothiophenol (4-ATP) and cultured, immersing the electrode in a first solution and then applying a voltage; and c) immersing the electrode of said step b) in a second solution and then applying a voltage.

In the present invention, the washing the electrode with sulfuric acid in said step a) may be 1 to 3 hours, and preferably 2 hours, but is not limited thereto. If the electrode is washed for less than 1 hour or more than 3 hours, the surface of the electrode cannot be etched sufficiently.

In the present invention, the electrode for a biosensor may be for measuring NADH (reduced form of nicotinamide adenine dinucleotide).

In the present invention, the "biosensor" refers to an analytical device that combines a biological component or a substance capable of reacting with an analyte with a physicochemical detector, and is used for the detection of analytes. By biologically engineering sensitive biological elements, biologically fractionated samples, etc., signals resulting from the interaction with the analyte are converted to more easily measure and quantify. For the purposes of the present invention, the substance capable of reacting with the analyte may be N-phenylquinone diimine for measuring NADH (reduced form of nicotinamide adenine dinucleotide).

Further, in the present invention, said sulfuric acid in said step a) may have a molar concentration of 5 mM to 15 mM, and preferably of 10 mM, but is not limited thereto. If the molar concentration of sulfuric acid is lower than 5 mM or higher than 15 mM, the surface of the electrode may not be etched sufficiently or the electrode may be corroded.

In the present invention, said "4-aminothiophenol (4-ATP)" is an organic substance capable of forming a self-assembled monolayer, which is a regularly well-ordered organic molecular film spontaneously coated on the surface of the electrode, and the proportion of NADH contained in a sample can be measured through a process in which the state of $NH_2$ of said 4-aminothiophenol is changed by electrons generated during NADH oxidation and reduction processes.

In the present invention, the first solution and the second solution may be a phosphate buffer solution (PBS). For the purposes of the present invention, the first solution may be a phosphate buffer solution of a molar concentration of 90 mM to 100 mM and the second solution may be a phosphate buffer solution of a molar concentration of 5 mM to 15 mM, but the present invention is not limited thereto. As described above, if an electropolymerization reaction is performed by varying the molar concentrations of the first solution and the second solution, not only can the contact angle between N-phenylquinone diimine and the electrode be brought down to 39° from 48° through the stabilization of electric current flow but the electrode can also be reused up to 20 times. Furthermore, in the present invention, if the molar concentration of the first solution is lower than 90 mM or higher than 100 mM, imine cannot be generated sufficiently, and if the molar concentration of the second solution is lower than 5 mM or higher than 15 mM, the contact angle cannot be sufficiently reduced as desired by the present invention.

In the present invention, if the contact angle of N-phenylquinone diimine is decreased as described above, N-phenylquinone diimine that can be bonded to the surface of the electrode increases significantly, thereby making the reaction with NADH active, which leads to the sensitivity of the electrode, thus providing an advantage that NADH can be detected even when a trace amount of NADH is present in a sample.

In the present invention, said "cyclic voltammetry" is one of the methods that can directly determine what kind of reaction is occurring on the surface of an electrode, and refers to scanning a potential by repeating several times a method of recording the flowing current in the current-potential curve when sweeping the potential in proportion to time. For the purpose of the present invention, the applying a voltage in said steps b) and c) may be performed by cyclic voltammetry and preferably, may be to sweep a potential from 0.8 to −0.4 V, but is not limited thereto.

In an embodiment of the present invention, the electrode in accordance with the present invention may comprise one or more kinds selected from a group consisting of gold, aluminum, platinum, nickel, graphene, silver nanowire films, carbon, metal grids, and indium tin oxide. Preferably, the electrode may be gold, but is not limited thereto.

Another implementation of the present invention provides an electrode for a biosensor for NADH measurement produced by the manufacturing method in accordance with the present invention.

In the above description of the present invention, the details of the electrode, the biosensor, cyclic voltammetry, the first solution, and the second solution are the same as those described in the manufacturing method, and accordingly, the detailed description thereof will be omitted below.

Yet another implementation of the present invention provides a biosensor comprising the electrode in accordance with to the present invention.

In the biosensor of the present invention, the details of the electrode, the biosensor, cyclic voltammetry, the first solution, and the second solution are the same as those described in the manufacturing method, and accordingly, the detailed description thereof will be omitted below.

In the present invention, the biosensor may be more suitable for measuring NADH (reduced form of nicotinamide adenine dinucleotide) for the purposes of the present invention.

The biosensor of the present invention may further comprise a bio-transducer, an electronic system including an amplifier, a processor, and a display, and so on that may be typically included in a biosensor, in addition to the electrode in accordance with the present invention.

In an embodiment of the present invention, the biosensor can measure the value of NADH in a sample through a process of converting imines in N-phenylquinone diimine bonded to the surface of the electrode into amines by electrons generated during the oxidation of NADH contained in the sample, of measuring the electrons generated when converting them back to imines, and of converting it into a quantifiable value. The full function of mitochondria has been required in the related art in which the oxidation-reduction reaction of NADH is measured through the reaction with dehydratases inside the mitochondria through a color reaction such as the WST-1 or MTT assay; however, with the measurement method as described above, the electrode produced by the manufacturing method in accordance with the present invention does not need dehydratases since the measurement method of the biosensor corresponds to a first-order reaction rather than an enzymatic reaction, and it may be possible to measure cell viability through quantitative measurement of NADH discharged into the media upon cell death.

FIG. 7 shows a schematic diagram of a process of measuring NADH in a sample using the biosensor in accordance with the present invention, which will be described in detail below with reference to the drawing.

As shown in FIG. 7(a), in order to measure the presence of NADH in blood, a process of measuring and quantifying the number of electrons emitted to the biosensor including the electrode in accordance with the present invention may be performed without going through a separate sample pretreatment process, after extracting the sample of a target of interest.

Moreover, as shown in FIG. 7(b), in order to measure the amount of NADH produced by apoptosis, media of target cells are injected into the biosensor including the electrode in accordance with the present invention, and then a process of measuring and quantifying the number of electrons emitted may be performed to thereby measure the extent of apoptosis.

The electrode produced by the manufacturing method described above in accordance with the present invention has a significantly higher degree of bonding of N-phenylquinone diamine than the electrode of the related art, which in turn leads to higher sensitivity enough to measure even a small amount of NADH contained in the sample, and thus there is an advantage of enabling measurement without going through a separate sample pretreatment process as in the procedure described above.

Effects of the Invention

The electrode produced by the method in accordance with the present invention can not only stabilize the current flow during an electropolymerization reaction but also make the contact angle significantly smaller, thereby increasing the efficiency of surface modification. Moreover, it is possible to reuse the electrode used for the biosensor several times through the process as described above.

In addition, when the electrode in accordance with the present invention is used in a biosensor, by maintaining sensitivity and selectivity without interference, there are advantages that it is possible to measure a target of interest even in blood or serum that has not undergone a pretreatment process corresponding to a trace amount, to measure cell viability continuously and in real-time, and to be applicable to the field of cytotoxicity. Furthermore, cell viability can be measured in apoptotic cells that have lost the function of mitochondria by measuring NADH secreted into the serum.

DETAILED DESCRIPTION OF EMBODIMENTS

Hereinafter, the present invention will be described in more detail by way of embodiments. These embodiments are merely for describing the present invention in greater detail, and it will be apparent to those having ordinary skill in the art that the scope of the present invention is not limited by these embodiments in accordance with the subject matter of the present invention.

Embodiments

Production Example

Production of Electrode for Biosensor for NADH Measurement

An electrode suitable for a biosensor for NADH measurement was produced by performing the following steps.

A gold (Au) electrode was washed with sulfuric acid ($H_2SO_4$) of a molar concentration of 10 mM. Then, in order to form a self-assembled monolayer, the electrode was immersed in 4-aminothiophenol prepared at a molar concentration of 10 mM, and then cultured for 2 hours. Thereafter, N-phenylquinone diimine (hereinafter, referred to as 'NPQD') was formed through a process in which the electrode was immersed in a phosphate buffer solution of a molar concentration of 100 mM (high concentration) and then a voltage was swept for a potential between 0.8 V and −0.4 V in cyclic voltammetry. After immersing the electrode having said NPQD formed thereon in a phosphate buffer solution of a molar concentration of 10 mM (low concentration), a process of sweeping a voltage is performed once again by applying the same voltage as the step of forming NPQD in the phosphate buffer solution of 100 mM, to finally produce an electrode in accordance with the present invention.

Comparative Example

Production of Electrode

For comparison with Production Example above, a process of modifying the surface of an electrode was performed using only a phosphate buffer solution of high concentration. Specifically, a gold (Au) electrode was washed with sulfuric acid ($H_2SO_4$) of a molar concentration of 10 mM. Then, in order to form a self-assembled monolayer, the electrode was immersed in 4-aminothiophenol prepared at a molar concentration of 10 mM, and then cultured for 2 hours. Thereafter, NPQD was formed through a process in which the electrode was immersed in a phosphate buffer solution of a molar concentration of 100 mM (high concentration) and then a voltage was swept for a potential between 0.8 V and −0.4 V in cyclic voltammetry.

[Embodiment 1] Measurement of Contact Angle of 4-aminothiophenol (4-ATP)

Changes in the contact angle of NPQD, formed on the surfaces of the electrodes according to Production Example above, were checked. Specifically, after dropping 10 μl of distilled (DI) water on the electrodes of Production Example above at room temperature and humidity condition of 46%, photographs of the respective electrodes were taken, and the measurement and analysis of the contact angle were performed using the method provided by the manufacturer through IMAGE J software, thereby showing the results in FIGS. 1 and 2.

Figure 1:
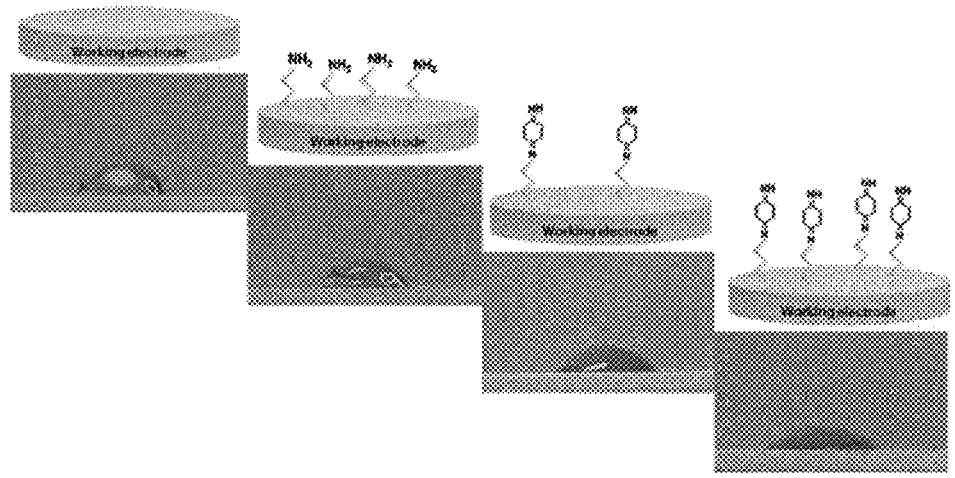
FIG. 1 shows a schematic diagram of the modified surface of an electrode and results of the measurements of the degree of hydrophilicity, in accordance with an embodiment of the present invention.
Figure 2:
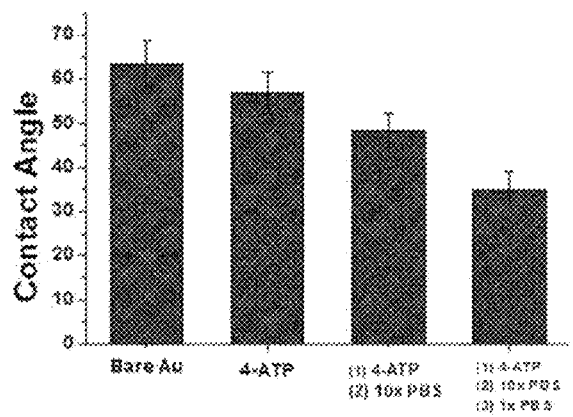
FIG. 2 shows a graph of the measurements of the contact angle of imine that appears upon surface modification, in accordance with an embodiment of the present invention.

As shown in FIGS. 1 and 2, NPQD bonded to the surface of Production Example was able to be bonded to the surface in a larger amount, and through this, it can be seen that the surface of the electrode was converted to be more hydrophilic. In particular, as shown in FIG. 2, Comparative Example showed little change in its contact angle compared with the case of bonding only 4-aminothiophenol, whereas in the case of Production Example, the contact angle was significantly lowered from 55° to 39°.

From the above results, it can be seen that Production Example in accordance with the present invention can significantly lower the contact angle of NPQD, thereby making the surface hydrophilic, through the two steps of reactions with a high concentration and low concentration of a phosphate buffer solution.

Figure 3:
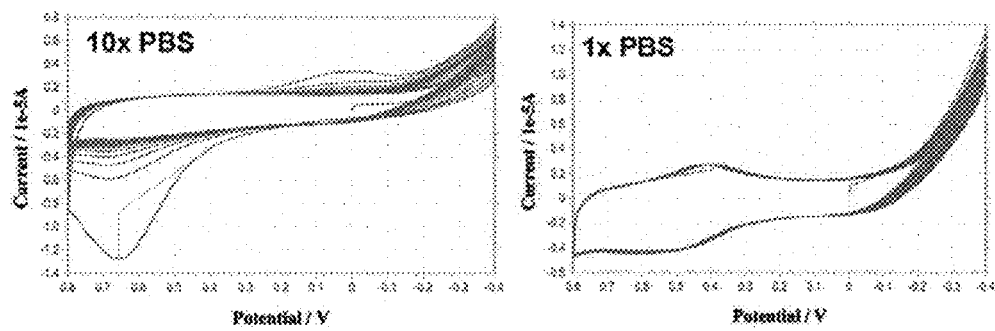
FIG. 3 shows the results of the measurements of the cyclic voltage-current by the concentration of a phosphate buffer solution, in accordance with an embodiment of the present invention.

[Embodiment 2] Measurement and Comparison of Stabilization of Electric Current Values In order to compare whether the phosphate buffer solution of a high concentration (100 mM) and the phosphate buffer solution of a low concentration (10 mM) stabilize electric current values, an electrochemical analysis was performed according to the protocol provided by the manufacturer using a multi-potentiostat device of the CH1040C series, thereby showing the results in FIG. 3.

As shown in FIG. 3, the measured electric current values were relatively unstable in the phosphate buffer solution of high concentration, whereas the electric current values exhibited a very stable graph in the phosphate buffer solution of 10 mM, corresponding to a low concentration.

From the above results, it can be seen that performing polymerization reactions in different steps with the conditions of high and low concentrations in producing Production Example in accordance with the present invention leads to the stabilization of electric current values.

[Embodiment 3] Measurement of Electrode Surface

Figure 4:
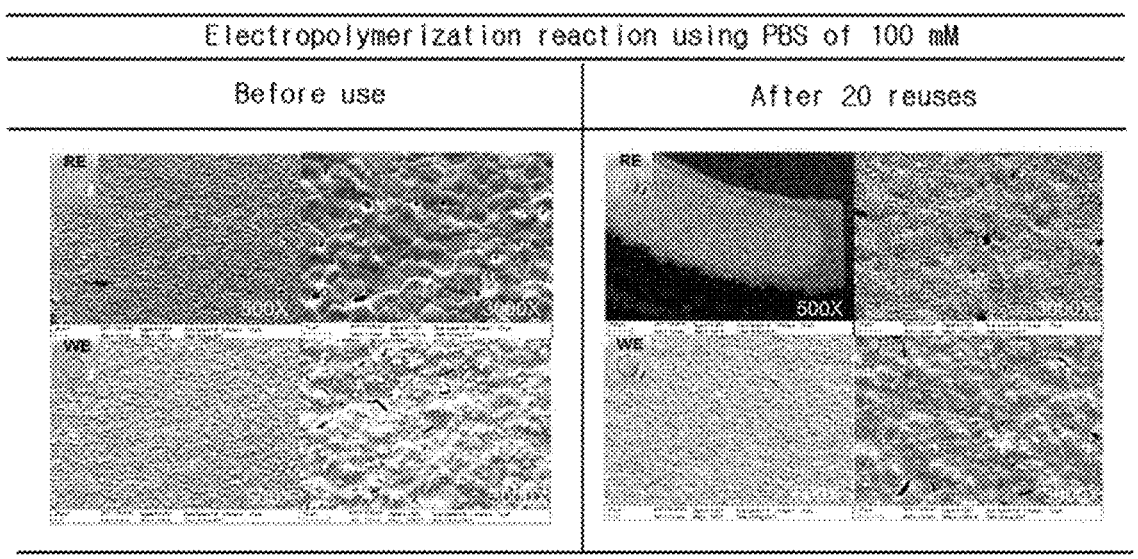
FIG. 4 shows the results of performing image analysis by an SEM on the surface of an electrode, in accordance with an embodiment of the present invention.
Figure 5:
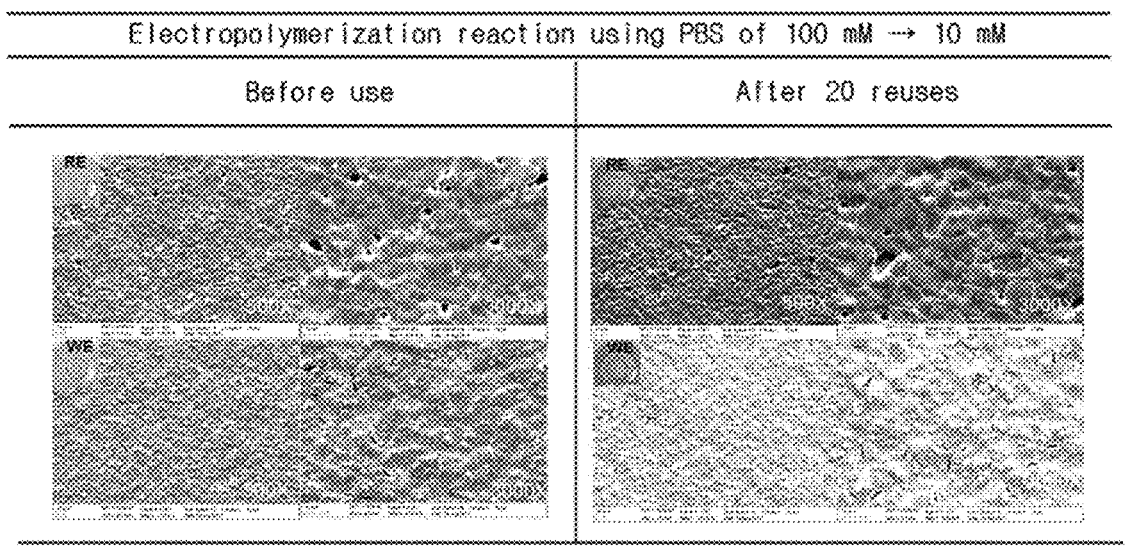
FIG. 5 shows the results of performing image analysis by an SEM on the surface of an electrode, in accordance with an embodiment of the present invention.

When NADH was measured several times in a biosensor comprising Production Example and Comparative Example, changes in the electrode surface were measured with a scanning electron microscope (SEM), and the results are shown in FIGS. 4 and 5. Here, the electrodes were subjected to a sputtering process to a thickness of 10 nm for scanning electron microscopy.

In addition, the measurement of NADH using the biosensor was performed through a process of inserting a sample containing NADH into the biosensor, followed by measuring the final value of the current generated by applying a voltage of −600 mV for 10 seconds.

As shown in FIG. 4, Comparative Example shows that NPQD was well produced in both the reference electrode (RE) and the working electrode (WE) sites; however, in the case of measuring after 20 reuses, the surface was rapidly deteriorated after it was used for NADH measurement multiple times in both the reference electrode and the working electrode sites.

On the other hand, as shown in FIG. 5, not only was NPQD well produced in both the reference electrode and the working electrode sites, but the degree of deterioration of the surface was also significantly lower even after 20 reuses, in the case of Production Example.

From the above results, it can be seen that the electrode of Production Example in accordance with the present invention can be reused a number of times in measurement when applied to a biosensor.

[Embodiment 4] Results of NADH Sensitivity Measurements

In order to compare the sensitivity of the NADH measurement between Production Example and Comparative Example, NADH in the sample was measured through the same method as in Embodiment 3 described above, and the results are shown in FIG. 6.

Figure 6:
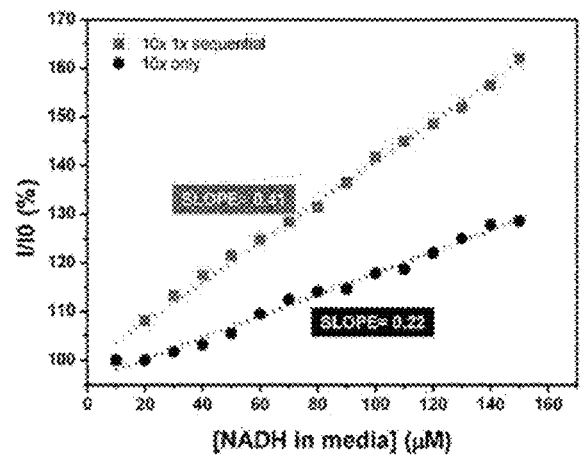
FIG. 6 shows NADH measurement values by concentration, using an electrode in accordance with an embodiment of the present invention.
Figure 7A:
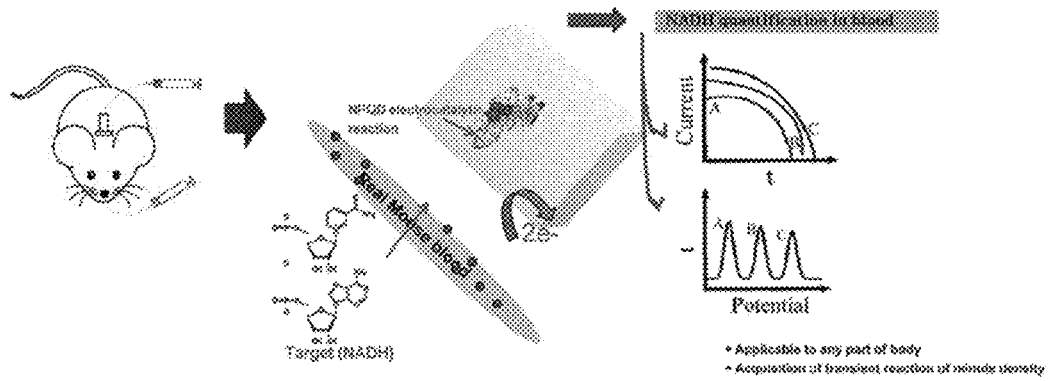
FIGS. 7(a) and (b) show schematic diagrams of an NADH measurement process using a biosensor for NADH measurement in accordance with an embodiment of the present invention.
Figure 7B:
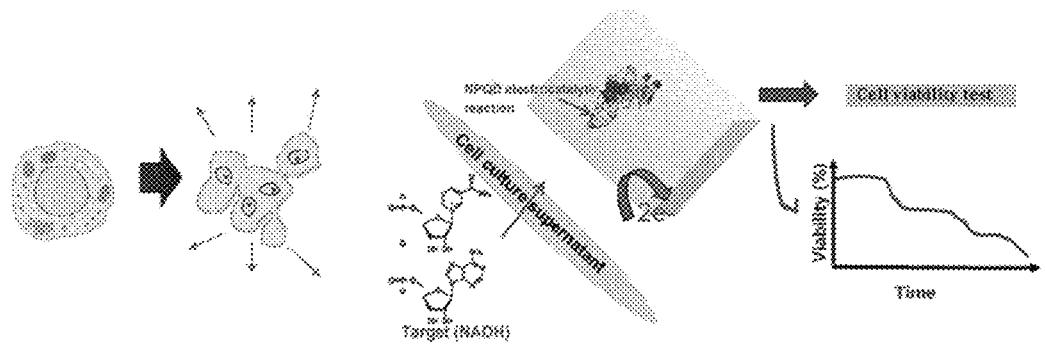

As shown in FIG. 6, the NADH measurement value of 100 μM corresponded to about 140% for Production Example, whereas a value corresponding to 110% was measured in Comparative Example, and the NADH measurement value of 140 μM corresponded to about 155% for Production Example, whereas it was measured at a significantly lower level of about 120% in the case of Comparative Example.

From the above results, it can be seen that when measuring NADH using Production Example in accordance with the present invention as an electrode, the sensitivity is significantly higher than that of Comparative Example.

While the present invention has been described in detail above, the scope of the present invention is not limited thereto, and it will be apparent to those having ordinary skill in the art that various modifications and changes can be made without departing from the spirit of the present invention as set forth in the claims.

What is claimed is:

1. A method for manufacturing an electrode for a biosensor, comprising:
   a) washing the electrode with sulfuric acid;
   b) after the electrode of said step a) is placed in 4-aminothiophenol (4-ATP) and cultured, immersing the electrode in a first solution and then applying a voltage; and
   c) immersing the electrode of said step b) in a second solution and then applying a voltage;
   wherein the first solution in said step b) is a phosphate buffer solution of a molar concentration of 90 mM to 100 mM; and
   wherein the second solution in said step c) is a phosphate buffer solution of a molar concentration of 5 mM to 15 mM.

2. The method for manufacturing an electrode of claim 1, wherein the voltage in said steps b) and c) is applied by cyclic voltammetry.

3. The method for manufacturing an electrode of claim 2, wherein in said steps b) and c), said cyclic voltammetry is to sweep a potential from 0.8 to −0.4 V.

4. The method for manufacturing an electrode of claim 1, wherein the electrode for a biosensor is for measuring NADH (reduced form of nicotinamide adenine dinucleotide).

5. The method for manufacturing an electrode of claim 1, wherein the electrode comprises one or more kinds selected from a group consisting of gold, aluminum, platinum, nickel, graphene, silver nanowire films, metal grids, carbon, and indium tin oxide.

6. An electrode for a biosensor for NADH measurement by the method for manufacturing of claim 1.

7. A biosensor comprising the electrode of claim 1.

8. An electrode for a biosensor for NADH measurement by the method for manufacturing of claim 2.

9. An electrode for a biosensor for NADH measurement by the method for manufacturing of claim 3.

10. An electrode for a biosensor for NADH measurement by the method for manufacturing of claim 4.

11. An electrode for a biosensor for NADH measurement by the method for manufacturing of claim 5.

12. A biosensor comprising the electrode of claim 2.

13. A biosensor comprising the electrode of claim 3.

14. A biosensor comprising the electrode of claim 4.

15. A biosensor comprising the electrode of claim 5.

* * * * *